United States Patent [19]

Hubbard

[11] Patent Number: 5,388,577
[45] Date of Patent: Feb. 14, 1995

[54] ELECTRODE ARRAY MICROCHIP

[75] Inventor: Allyn E. Hubbard, Milton, Mass.

[73] Assignee: Boston University, Boston, Mass.

[21] Appl. No.: 57,692

[22] Filed: May 4, 1993

Related U.S. Application Data

[60] Continuation of Ser. No. 809,089, Dec. 10, 1991, abandoned, which is a division of Ser. No. 535,889, Jun. 8, 1990.

[51] Int. Cl.[6] .................. H01L 23/48; A61B 5/04
[52] U.S. Cl. .................. 128/639; 257/448; 257/784; 257/734; 128/642; 128/640; 128/644
[58] Field of Search ............ 257/734, 784, 736, 448; 126/639, 640, 642, 644

[56] References Cited

U.S. PATENT DOCUMENTS

| | | | |
|---|---|---|---|
| 4,319,264 | 3/1982 | Gangulee et al. | 357/65 |
| 4,499,440 | 2/1985 | Grudkowski | 357/65 |
| 4,589,191 | 5/1986 | Green et al. | 357/65 |
| 4,597,167 | 7/1986 | Moriya et al. | 357/65 |
| 4,628,338 | 12/1986 | Nakayama et al. | 357/65 |
| 4,821,094 | 4/1989 | Okazaki et al. | 357/65 |
| 4,924,276 | 5/1990 | Heime et al. | 357/65 |
| 4,947,114 | 8/1990 | Schindlbeck | 357/65 |
| 4,969,468 | 11/1990 | Byers et al. | 128/642 |
| 5,593,304 | 6/1986 | Slayman et al. | 357/65 |

*Primary Examiner*—Viet Q. Nguyen
*Attorney, Agent, or Firm*—Choate, Hall & Stewart

[57] ABSTRACT

An electrode array microchip, fabricated preferrably using CMOS technology, comprising electrodes made with overglass cuts over metal2 regions is disclosed. Overglass cuts of dimensions approximately an order of magnitude smaller than dimensions quoted in current design rules for CMOS technology are successfully employed to make exposed electrodes of dimensions on the order of microns. Thus, the electrode array chip can be produced cheaply on commercial fabrication lines. The invention finds many uses in biology and medicine, particularly when applied to the measurement of neural electrical activity.

12 Claims, 3 Drawing Sheets

ELECTRODE ARRAY MICROCHIP

This invention was made with government support under grant 2S07RR0743-25, awarded by the National Institutes of Health. The government has certain rights in the invention.

This is a continuation of copending application Ser. No. 07/809,089 filed on Dec. 10, 1991, now abandoned, which is a division of Ser. No. 07/535,889, filed on Jun. 8, 1990.

BACKGROUND OF THE INVENTION

The study of interconnected neural systems is crucial to understanding neural function. Until recently, attempts to measure electrical activity in neural networks have been pursued using either multiple single micropipettes, multibarrelled micropipettes, or single electrodes which record simultaneously from multiple sources of activity. However, these methods are unsuitable for recording from large numbers of neurons simultaneously.

For approximately the past twenty years, sporatic efforts have been undertaken to use integrated technology to record from collections of neurons. An example of such an effort is described in "An integrated-circuit approach to extracellular microelectrodes," by K. D. Wise et al, in *IEEE Transactions on Biomedical Engineering*, Vol. 17, July 1970. However, technical achievements in electrode fabrication technology have not been used extensively in the biological applications area. One reason for this is that high-technology electrode designs and fabrication techniques are generally unavailable outside of a small group of original developers. Furthermore, probe chips for biological applications are generally not designed to be made in commercial silicon foundries for reasons related to mechanics (e.g. pointed probes) and tissue compatibility (e.g. special materials).

One prior approach to making microelectrode arrays has been to use thin-film microlithography techniques to deposit gold electrodes on a glass substrate, as described in "Recording action potentials from cultured neurons with extracellular microcircuit electrodes," by J. Pine, in *Journal of Neuroscience Methods*, Vol. 2, 1980, and in "Recording from the Aplysia abdominal ganglion with a planar microelectrode array," by J. L. Novak and B. C. Wheeler, in *IEEE Transactions on Biomedical Engineering*, Vol. 33, February 1986. Resulting electrode dimensions have been on the order of 10-25 microns. Another approach has employed special methods adapted from integrated-circuit fabrication techniques, as described in "A high-yield IC-compatible multichannel recording array," by K. Najafi et al, in *IEEE Transactions on Electron Devices*, Vol. 32, July 1985. In this probe, an array of gold electrodes was supported on a silicon carrier. By selectively removing an insulating layer of silicon dioxide which covers the probe, the effective electrode-tip diameters were made as small as 2 microns in diameter. The design was compatible with incorporation of on-chip circuitry.

In these prior approaches, the issue of biocompatibility has been an important consideration, leading to use of special materials (gold for example). For cases where biocompatibility is not an important issue, such as in short-term experiments, there is a need for a cheap standard microelectrode array microchip. To meet these goals, a design is required that can be made on a commercial fabrication line.

SUMMARY OF THE INVENTION

The electrode array microchip according to the present invention uses standard fabrication line techniques and comprises metal regions on a substrate over which an overglassing material has been applied. The overglass is cut to expose metal, thereby forming electrodes. The electrodes are electrically connected to wire bonding or probe pads or to integrated circuitry within the microchip.

The electrode array chip is fabricated, in a preferred embodiment, using standard CMOS fabrication technology. The electrodes are formed by making overglass cuts above metal2, the metal layer directly beneath the overglass in standard CMOS technologies. In microchip fabrication handbooks, overglass cuts of less than approximately 60 microns in width are not described in the design rules. In creating the present invention, it was discovered that overglass cuts of significantly smaller dimension are possible using commercial CMOS fabrication techniques. The result is new design rules, the use of which is a key part of the present invention.

The use of standard fabrication methods has two advantages. First, the chips can be made cheaply, rendering them essentially disposible. Second, the chips can be made readily available to all workers in a given field. Thus researchers can directly compare results with their colleagues. Also, workers can develop and share standard techniques using the chip.

The present invention can be adapted for many scientific and medical applications. One important application of the electrode array chip is in research directed to the measurement of electrical activity of neural networks. The chip can also be used actively to electrically stimulate cells while simultaneously recording the resulting activity. Stimulation with electric current can also be used to affect cell development, for example, in conditioning embryonic skeletal muscle tissue to become cardiac muscle. Another application of the chip is as a device for electrophoresis, allowing precise separation of molecules with an appropriate layout of electrodes. Mounted on an extender, the chip can also be incorporated in a tool for brain surgeons to record and analyze brain activity.

DESCRIPTION OF THE PREFERRED EMBODIMENTS

Fabrication of the invention

Figure 1:
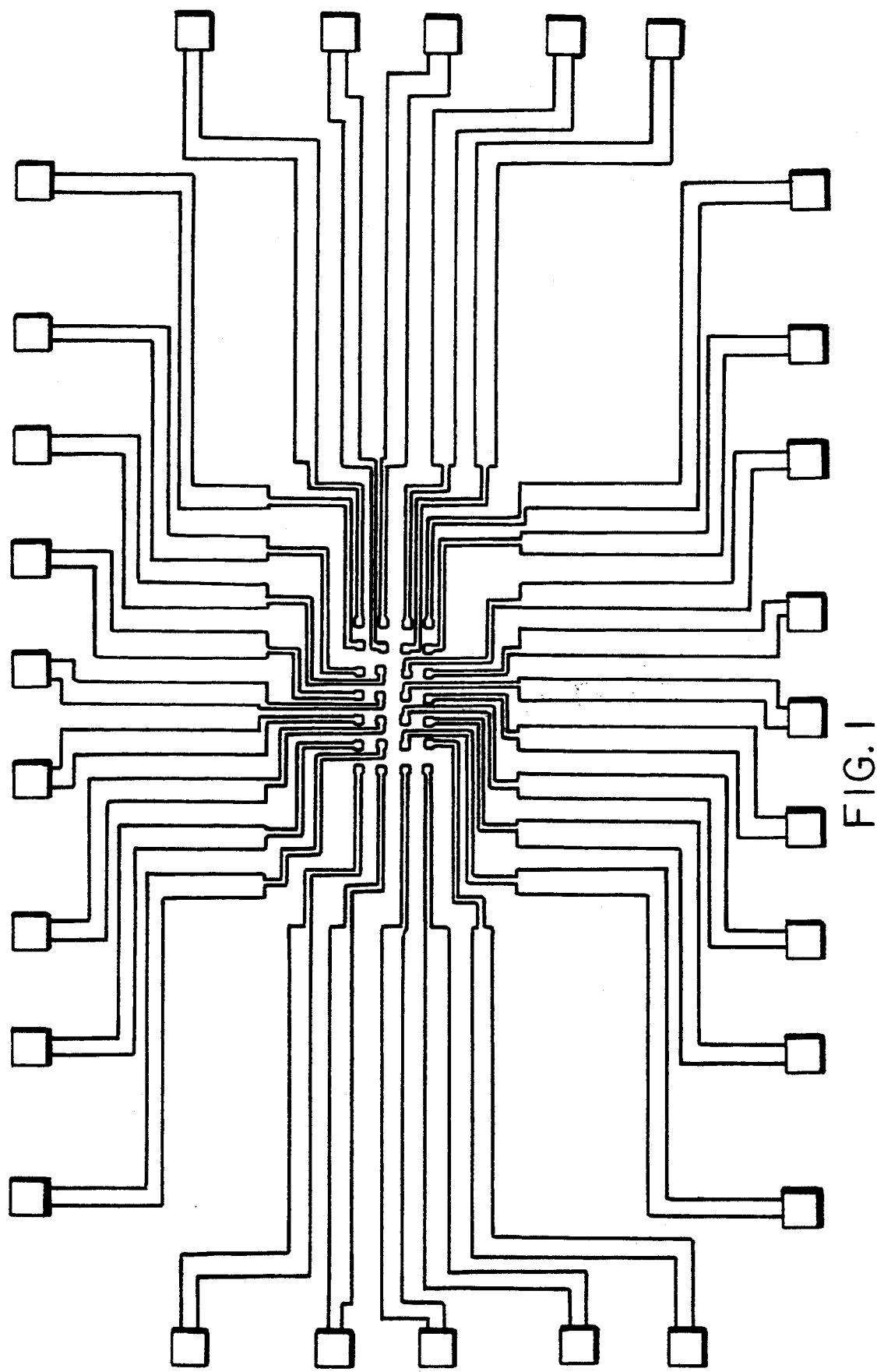
FIG. 1 shows one embodiment of the electrode array microchip of the present invention, which was used to determine design rules for further array design.

A microchip fabricated using CMOS technology consists of layers of conducting, insulating, and semiconducting materials. The fabrication process involves the geometric patterning of each layer and the geometric patterning of the sequence of layers in order to implement a given integrated system. The process is described in detail in *Introduction to VLSI systems*, by C. Mead and L. Conway, Addison-Wesley Publishing Company, Reading Mass., 1980. Silicon dioxide is commonly used as an insulating material in the CMOS process. In patterning a layer of silicon dioxide, a continous layer of silicon dioxide is applied to an underlying layer (usually silicon or metal), followed by a thin film of an organic resist. The pattern for the silicon dioxide layer initially exists as a mask, a transparent material coated with a thin layer of opaque material in sections corresponding to the desired pattern. The mask is placed over the layer of resist-coated silicon dioxide, and then the chip is irradiated with intense ionizing radiation, causing the resist to break down in the exposed sections. These areas of affected resist are then dissolved away with a suitable solvent. Finally the chip is exposed to a material that will etch silicon dioxide, but not affect other materials of the chip. After the remaining resist is removed, the desired pattern is etched in the silicon dioxide, exposing the substrate below.

As a final step in standard fabrication line chip manufacture, the chip surface is coated with a layer of silicon dioxide to provide protection for the finished chip. This step is called overglassing. To expose contact cuts at the locations of the metal wire bonding pads, a mask is used as described above.

Standard fabrication line techniques are pattern independent. For this to be so, the microchip designer requires a precise specification of the capabilities of the processing line. This specification takes the form of a set of design rules which define minimum allowable constraints for widths, separations, extensions and overlaps that are within the resolution of the process.

In the past, the only reason for making cuts in the overglass has been to expose contact areas to attach wires or probes. As the wire bonding pads and probing pads are relatively large, on the order of 60–100 microns, current design rules for overglass cuts are also relatively large. For example, in the *CMOS3 Cell Library* by D. V. Heinbruch, Addison-Wesley, Reading, Mass., 1988, bonding pad openings in the overglass layer are specified to be 90×90 microns and probing pad openings are specified to be 65×65 microns. In the MOSIS Scalable and Generic CMOS Design Rules, February 1988, Revision 6, the bonding pad openings are specified to be 88×88 microns and probing pad openings are specified to be 63×63 microns. For both bonding and probing pads, the pad overlap of glass is specifed to be 6 microns on each edge. Thus, the metal2 bonding pads are 100×100 microns and the metal2 probing pads are 75×75 microns. The pad space to unrelated metal2 is 30 microns.

A salient feature of the present invention is that the electrodes are created by overglass cuts above metal2. Therefore a major step in the development of the invention was determining whether small and accurately placed overglass cuts could be made reliably using a standard fabrication process. In the absence of the appropriate data or design rules regarding overglass cuts smaller than approximately 60 microns, experiments were performed to determine how small electrodes could be accurately fabricated. Test chips were designed by the present inventor and fabricated by the MOSIS fabrication service, which makes standard CMOS fabrication available through grants to universities. The chip designs contained specifications for overglass cuts smaller than 63 microns, a design rule error that the service was instructed to ignore.

Figure 2:
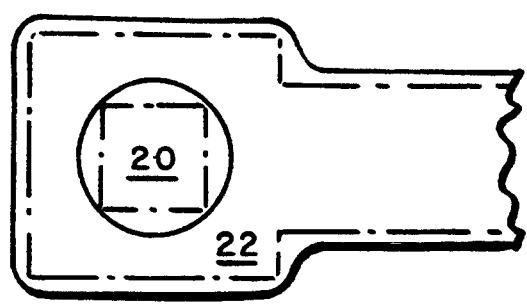
FIG. 2 shows a schematic view of an overglass cut over a metal2 pad.

One of the test chip designs was an array having 28 metal2 pads of size 16 lambda (lambda=1.5 microns for the fabrication technology used), which had overglass cuts sized from one to seven lambda. This electrode array chip is shown in FIG. 1. On microscopic examination of the fabricated chip, it was discovered that overglass cuts of one lambda did not fabricate. Overglass cuts of two to three lambda typically fabricated into roughly 20% bloated circles with variation on the order of one-half micron. Larger cuts were rounded. Thus, it was discovered that overglass cuts, of dimension approximately an order of magnitude smaller than dimensions specifed in the design rules, can be made to expose an underlying metal2 layer, thus forming an electrode, using standard fabrication technologies. A schematized glass cut 20 centered over a metal2 pad 22 is illustrated in FIG. 2. The designed boundaries are shown as orthogonal lines, while the fabricated boundaries curve gradually.

Another of the test chip designs was an array having six lambda metal2 pads with four lambda overglass cuts spaced from three to six lambda. Glass cut spacings as small as three lambda were fabricated cleanly, however, in this case, the underlying one lambda spaced metal was fused.

The alignment of glass cuts over metal2 areas is also of importance because the full area of a cut should be exposed to metal2 for good electrode function. For two lambda glass cuts, a systematic misalignment of the cut relative to the pad of about 0.3 microns, with a standard error of about 0.5 microns, was found. Because the smaller glasscuts are typically 20% bloated circles, it is anticipated that small glasscuts drawn within metal2 areas which are larger than the cuts by one lambda on all sides will sometimes extend beyond the edge of the metal2 when fabricated.

Figure 3:
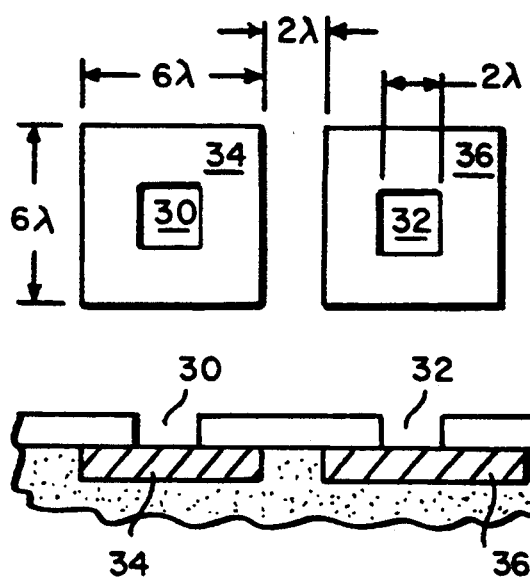
FIG. 3 shows a cut-away side view and a top view of two adjacent electrodes of an electrode array fabricated according to the minimum design rules of the present invention.

The final result of the experiments is the demonstration that an electrode array can be fabricated using standard CMOS techniques by ignoring standard design rules, provided one uses overglass cuts of at least two lambda centered over metal2 regions of at least six lambda separated by at least two lambda. A section of such an array consisting of two adjacent electrodes with glass cuts 30 and 32 and metal2 regions 34 and 36 is illustrated in FIG. 3 in a cut-away side view and in a top view. This figure illustrates a minimum dimension array which can be fabricated using current CMOS technology. However, all electrode arrays made with overglass cuts smaller than those specified in the currently-accepted design rules (see, for example, Heinbruch, 1988) are within the scope of the present invention.

Although with present microchip fabrication technology the use of a CMOS fabrication line is the most appropriate for making the chip of the present invention, it will be apparent to those skilled in the art that the methods are also applicable to other technologies, such as nMOS and GaAs. It is not intended that the present invention be limited to the use of CMOS technology exclusively.

Applications of the invention

One important application of the electrode array chip is in research directed to the measurement of electrical activity of neural networks. For this application, the cells of interest can be cultured onto the array surface of the microchip while in an incubator, or deposited onto the array surface prior to the start of an experiment. In this way, recordings of the electrical activities of the cells can be made from each site on the cell membrane in contact with the cell membrane. For certain large-cell cultures, this method is far more practical than the current method of using a plurality of microelectrodes, each of which must be painstakingly applied to the cells individually. For small-cell cultures, the interconnected neural tissue is suspended in fluid 0–100 microns above the surface of the chip. In this case image reconstruction techniques, either on a second chip, or off-line, can be used to compute current sources and sinks based on the field potentials remotely sensed by the array. Another application of the electrode array chip is to create an on-line video image of propagating neural activity, using the sensor array as a component of a "camera".

Figure 4:
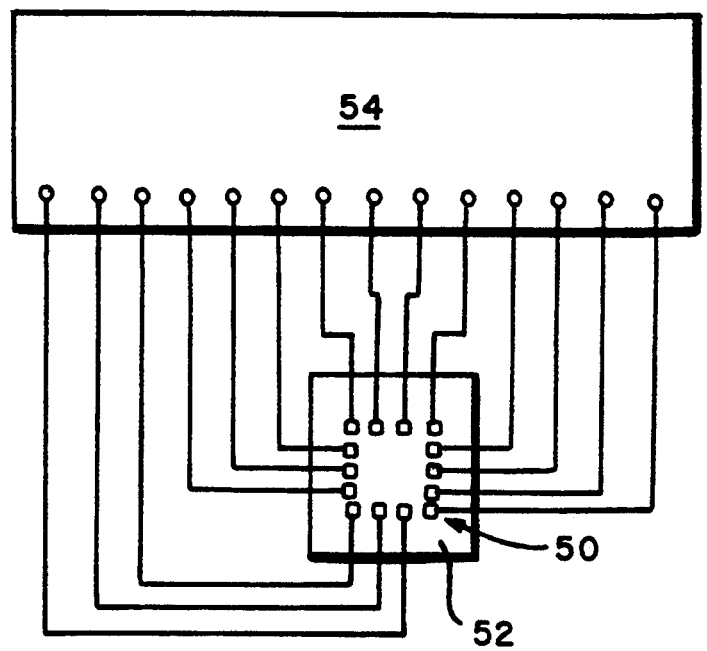
FIG. 4 shows the electrode array microchip of the present invention used as an active device by the connection of the electrodes to an appropriate voltage source.

Another use of the chip is to electrically stimulate cells. In this use of the chip as an active device, appropriate connection of the wire bonding pads 50 of the microchip 52 to programmed voltage sources 54 is required, as illustrated in FIG. 4. Exposure to electric fields is known to modify the develpment and growth of many cell types, particularly muscle cells. With the chip of the present invention, electric fields of a desired pattern can easily be applied to cells in an incubator by connecting the pads of the chip to an appropriate voltage source.

Another application of the chip used as an active device is as a tool for electrophoresis, a technique for separating molecules (proteins for example) by applying an electric field to a suspension of the molecules in a substrate (a gel for example). The charge of the molecules affect the direction and the magnitude of their migration in the field. The chip of the present invention provides a way to customize the route of the migrating molecules, allowing a more precise separation than in currently used electrophoresis techniques.

Figure 5:
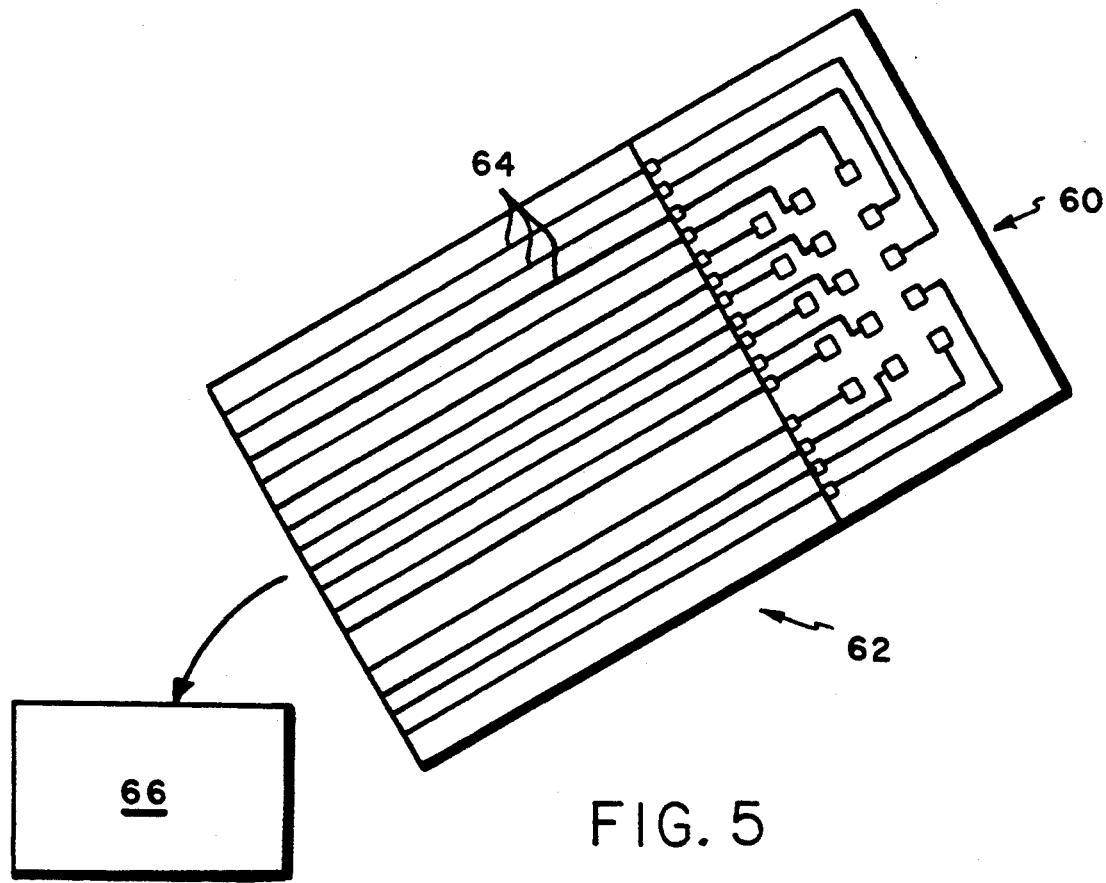
FIG. 5 shows a tool for recording brain activity employing the electrode array microchip of the present invention.

Yet another application of the chip involves its incorporation in a tool for brain surgeons to record and analyze brain activity. In its simplest embodiment, illustrated in FIG. 5, such a tool consists of simply the chip 60 attached to the end of a support structure 62 that contains wires 64 leading from the chip and allows the chip to be easily manipulated manually. When the wires 64 are connected to a display or recording device 66, the electrical signals detected by the electrodes can be observed. This device would allow surgeons to determine, for example, if brain tissue is alive or dead. In other embodiments, circuitry is incorporated on the chip and appropriate signal processing units are connected to the output of the tool, such that electrical brain activity can be monitored, and useful diagnostic information extracted.

Figures 6A, 6B:
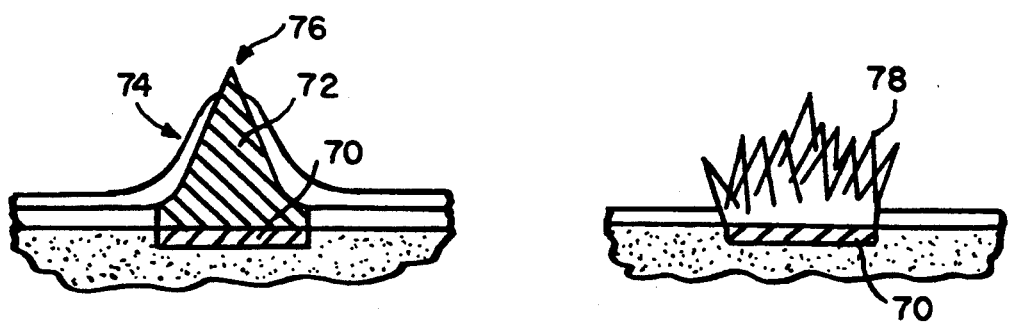
FIG. 6 shows embodiments of the present invention that provide pointed electrodes.

Although one of the great advantages of the present invention is its standard fabrication, follow-on customization of the probe surfaces for certain applications is possible. One such case is the addition of pointed probes extending from the planar electrodes of the array, as illustrated in two embodiments in FIG. 6. This customization of the basic chip design will lead to improved results in many applications of the chip. In FIG. 6A, a conducting material such as gold is deposited on the exposed electrodes 70 of the chip in order to form a point 72 of a desired sharpness and height above the chip. Then, the surface of the chip, including the points, is coated with an insulating material 74. Finally, this material is removed from the tips of the probes 76 by delivery of a brief current pulse. This configuration is desireable for intracellular recording from cells. In FIG. 6B, platinum black is electrochemically deposited on the electrodes 70 to form a thistle-like structure 78. Such an electrode surface on the tips of conventional electrodes can be used to create a superior-quality recording from nerve cells.

As will be clear to those skilled in the art, a large variety of additional applications of the present invention can be easily imagined, many of which may be outside the fields of biology and medicine. The scope of the invention is not intended to be limited to those examples described above.

I claim:

1. An electrode army microchip for receiving biological electrical signals comprising:

a plurality of substantially planar metal regions supported on a surface of a substrate, insulating material covering said plurality of metal regions and said surface, cuts in said insulating material, at least one of said cuts having a width of at least one micron, said cuts arranged to expose portions of said metal regions, whereby each exposed portion forms a substantially planar electrode for engagement with a biological material, and regions of metal electrically connected to said electrodes to form electrical connections from said electrodes to wire bonding or probe sites on a surface of said microchip or to integrated circuitry within said microchip, whereby biological electrical signals from said biological material detectable at said electrodes are transmitted to said wire bonding or probe sites or to said integrated circuitry.

2. A CMOS electrode array microchip for receiving biological electrical signals comprising:

a pattern of adjacently arranged and substantially planar metal regions on a surface of a substrate, adjacent regions separated by a distance, insulating material covering said pattern of metal regions and said surface, a plurality of cuts in said insulating material, said cuts arranged to expose portions of said metal regions, whereby each exposed portion forms a substantially planar electrode for engagement with a biological material, at least one cut of said plurality of cuts having a width of three microns, said width at least equal to the distance between two adjacent metal regions, and regions of metal electrically connected to said electrodes to form electrical connections from said electrodes to wire bonding or probe sites on a surface of said microchip or to integrated circuitry within said microchip, whereby biological electrical signals from said biological material detectable at said electrodes are transmitted to said wire bonding or probe sites or to said integrated circuitry.

3. The microchip of claims 1 or 2 wherein said insulating material is comprised of silicon dioxide.

4. The microchip of claims 1 or 2 wherein said substrate is comprised of silicon.

5. The microchip of claims 1 or 2 wherein said microchip comprises integrated circuitry.

6. The microchip of claim 5 wherein said integrated circuitry provides multiplexing means for electrical signals between the electrodes and wire bonding or probe pads.

7. The microchip of claims 1 or 2 attached to a support, whereby said support permits manual manipulation of said microchip.

8. The microchip of claim 7 further comprising means for electrically connecting said wire bonding or probe sites or said integrated circuitry of said microchip to a display or recording device, whereby said electrical signals are displayed or recorded.

9. The microchip of claims 1 or 3 further comprising a conducting material deposited on each said electrode, whereby the resulting electrode is made to extend to the surface or above the surface of said microchip.

10. The microchip of claim 9 wherein said conducting material is gold, deposited to form a point on each said electrode.

11. The microchip of claim 9 further comprising a post fabrication line insulating coating over the surface of said microchip, said coating being removed over a portion of each extended electrode, whereby effective electrode surface area is reduced.

12. The microchip of clam 9 wherein said-conducting material is platinum black electrochemically deposited on each said electrode, whereby effective electrode surface area is increased.

* * * * *

UNITED STATES PATENT AND TRADEMARK OFFICE
CERTIFICATE OF CORRECTION

PATENT NO. : 5,388,577
DATED : February 14, 1995
INVENTOR(S) : Allyn E. Hubbard

It is certified that error appears in the above-indentified patent and that said Letters Patent is hereby corrected as shown below:

In the Abstract, line 1: after "fabricated" please delete "preferrably" and insert therefor -- preferably --;

Column 6, line 9: please delete "desireable" and insert therefor -- desirable --;
Column 6, line 22: please delete "army" and insert therefor -- array --; and
Column 8, line 11: please delete "clam" and insert therefor -- claim --.

Signed and Sealed this

Third Day of October, 1995

BRUCE LEHMAN

Attest:

Attesting Officer

Commissioner of Patents and Trademarks